United States Patent
Klar-Barna et al.

(10) Patent No.: US 10,548,820 B2
(45) Date of Patent: Feb. 4, 2020

(54) COLORBLOCK LAYERED NAIL POLISH

(71) Applicants: Cindi Klar-Barna, New York, NY (US); Corey Barna, New York, NY (US)

(72) Inventors: Cindi Klar-Barna, New York, NY (US); Corey Barna, New York, NY (US)

( * ) Notice: Subject to any disclaimer, the term of this patent is extended or adjusted under 35 U.S.C. 154(b) by 178 days.

(21) Appl. No.: 15/587,644

(22) Filed: May 5, 2017

(65) Prior Publication Data

US 2018/0318180 A1  Nov. 8, 2018

(51) Int. Cl.
*A61K 8/03* (2006.01)
*A61Q 3/02* (2006.01)
*B65B 3/04* (2006.01)

(52) U.S. Cl.
CPC .............. *A61K 8/03* (2013.01); *A61Q 3/02* (2013.01); *B65B 3/04* (2013.01); *A61K 2800/43* (2013.01); *A61K 2800/87* (2013.01)

(58) Field of Classification Search
CPC .. A61K 8/03; A61K 2800/87; A61K 2800/43; B65B 3/04; B65B 29/00; B65B 2220/14; A61Q 3/02; B67C 3/023; G07F 13/06
See application file for complete search history.

(56) References Cited

U.S. PATENT DOCUMENTS 7,645,444 B2 *  1/2010  Malnou ................... A61K 8/03
424/64

OTHER PUBLICATIONS

Chouinard, M. M. "Updated! Review: Blackhead Beauty Stacked Nail Polishes". Lacquer or Leave Her! [online]. Feb. 24, 2013. [retrieved Mar. 16, 2019] Retrieved from the Internet <URL: http://lacquerorleaveher.blogspot.com/2013/02/review-blackheart-beauty-stacked-nail.html> (Year: 2013).*

Blue Cross Beauty Products Lay It on Me Nail Polish. Nails Magazine. Oct. 1, 2009. [retrieved on Mar. 15, 2019] Retrieved from internet <URL: https://www.nailsmag.com/product/20442/lay-it-on-me-nail-polish> (Year: 2009).*

* cited by examiner

*Primary Examiner* — Marina A Tietjen
(74) *Attorney, Agent, or Firm* — Ezra Sutton

(57) ABSTRACT

The present invention provides for a nail polish composition that is filled into a nail polish bottle, wherein the composition comprises a first nail polish layer comprising a first coloring material, which exhibits a first characteristic color, dissolved therein, and a second nail polish layer comprising a second coloring material, which exhibits a second characteristic color, dissolved therein. A first film layer formed over the first nail polish layer separates the first and second nail polish layers. Also, the first and second nail polish layers are disposed in the nail polish bottle at an angle relative to each other. In this manner, the first nail polish layer and the second nail polish layer are immiscible. Also, the first coloring material is insoluble in the second nail polish layer; and the second coloring material is insoluble in the first nail polish layer. Further, agitation of the nail polish composition causes the first and second nail polish layers to form an emulsion. The emulsion exhibits an apparent color that is different from the color of the first or second nail polish layers such that the apparent color is formed by combining the colors exhibited by the first and second coloring materials.

2 Claims, 1 Drawing Sheet

COLORBLOCK LAYERED NAIL POLISH

FIELD OF THE INVENTION

The present invention relates to a nail polish composition formed from different immiscible and separate layers of nail polish, wherein each separate layer exhibits a different color characteristic. More particularly, the present invention relates to a nail polish bottle that is filled at an angle(s) with different immiscible and separate layers of nail polish, wherein each separate layer exhibits a different color characteristic. This results in one nail polish bottle being filled with separate angular and layered blocks of different colored nail polish, which when agitated combine to form a nail polish color distinct from the individual nail polish layers in the bottle.

BACKGROUND OF THE INVENTION

It is known in the prior art that in order to obtain a wide variety or a unique nail polish color a user must carry multiple bottles each having different nail polish colors or a dual chambered nail polish bottle wherein an integral compartment wall in the bottle physically separates the different nail polishes. This is often necessary in order to blend or mix various nail polish colors in order to achieve a uniquely desired color.

However, carrying various nail polish bottles or bulky dual nail polish bottles is cumbersome and often requires mixing the various nail polish colors in an additional separate containers which can be messy. Thus, there is a need for a nail polish composition having a nail polish bottle that is filled at an angle(s) with different immiscible and separate layers of nail polish, wherein each separate layer exhibits a different color characteristic. This advantageously results in one nail polish bottle filled with separate angular and layered blocks of different colored nail polish, which when agitated combine to form a nail polish color distinct from the individual nail polish layers in the bottle.

DESCRIPTION OF THE PRIOR ART

Examples of various types of nail polish applicator bottles are described in prior art U.S. Pat. Nos., as follows: 5,826,741 to Dumler et al.; 5,810,497 to Bachmann et al.; D387,909 to Mattson; 5,655,554 to Goldberg; 5,645,090 to Juhl et al.; 5,638,837 to Juhl et al.; D363,375 to Arntsen; D353,101 to Desgrippes; D345,918 to Chevassus; D341,255 to Leone; D333,573 to Kamen; D331,697 to Desgrippes; D325,523 to Restrepo; 5,035,525 to Konose; 4,998,315 to Pessis; D311,258 to Jankewitz; 4,955,745 to Vauquelin; 4,944,318 to Gaylord, Jr. et al.; D308,635 to Dinunccio; 4,927,282 to Morane et al.; 4,917,520 to Reid et al.; D291,374 to Korper; D289,088 to Jankewitz; 4,640,637 to Winthrop; 4,635,657 to Stanford; D285,011 to Jankewitz; 4,454,622 to Poppendieck; 4,359,060 to Walker; and 4,194,617 to Bandell.

Also, examples of dual nail polish and cosmetic applicator bottles and containers are described in prior art U.S. Pat. No. 8,322,352 to Lampugnale; U.S. Pat. No. 6,120,202 to Donsky; U.S. Pat. No. 5,897,262 to Bratby-Carey; U.S. Pat. No. 5,655,554 to Goldberg; U.S. Pat. No. 5,052,839 to Pettengill; U.S. Pat. No. 4,600,328 to Elements; U.S. Pat. No. 2,691,184 to Miller; U.S. Pat. No. D220,864 to Weckman; U.S. Pat. No. D280,599 to Green; and U.S. Pat. No. D210,324 to Rapaz.

In addition, U.S. Pat. No. 6,627,181 to Busch, et al. discloses a multi layered nail polish composition having an enamel base coat top layer and a nail repair and adhesive bottom layer containing pigmented material. Thus, only the bottom layer contains pigmented colored material. Also, the two layers are separated gravity. The lighter, less viscous enamel base coat layer floats to the top of the bottle, while the heavier, more viscous, pigmented nail repair layer sinks to the bottom of the bottle.

However, none of these prior art patents provide for an improved nail polish composition formed from different immiscible and separate layers of nail polish, wherein each separate layer is filled at an angle(s) with different immiscible and separate layers of nail polish, wherein each separate layer exhibits a different color characteristic, and wherein when the various layers are agitated, they combine to form a nail polish color distinct from the individual nail polish layers in the bottle.

OBJECTS OF THE INVENTION

It is an object of the present invention to provide a nail polish composition formed from different immiscible and separate layers of nail polish, wherein each separate layer exhibits a different color characteristic.

Another object of the present invention is to provide a nail polish composition wherein when the various layers are agitated, they combine to form a nail polish color distinct from the individual nail polish layers in the bottle.

Another object of the present invention is to provide a nail polish composition formed from different immiscible and separate layers of nail polish, wherein each separate layer is separated from each other by a film layer.

Another object of the present invention is to provide a nail polish composition formed from different immiscible and separate layers of nail polish, wherein each separate layer is filled in the nail polish bottle at an angle.

SUMMARY OF THE INVENTION

The present invention provides for a nail polish composition that is filled into a nail polish bottle, wherein the composition comprises a first nail polish layer comprising a first coloring material, which exhibits a first characteristic color, dissolved therein, and a second nail polish layer comprising a second coloring material, which exhibits a second characteristic color, dissolved therein. A first film layer formed over the first nail polish layer separates the first and second nail polish layers. Also, the first and second nail polish layers are disposed in the nail polish bottle at an angle relative to each other. In this manner, the first nail polish layer and the second nail polish layer are immiscible. Also, the first coloring material is insoluble in the second nail polish layer; and the second coloring material is insoluble in the first nail polish layer. Further, agitation of the nail polish composition causes the first and second nail polish layers to form an emulsion. The emulsion exhibits an apparent color that is different from the color of the first or second nail polish layers such that the apparent color is formed by combining the colors exhibited by the first and second coloring materials.

DETAILED DESCRIPTION OF THE PREFERRED EMBODIMENT

Figure 1:
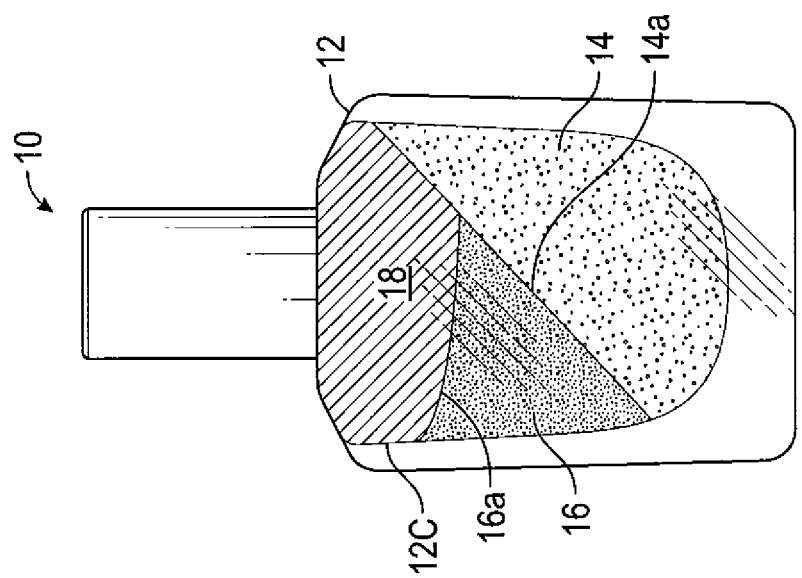
FIG. 1 is a perspective view of the nail polish composition in a nail polish bottle, showing a first nail polish layer and a second nail polish layer both filled in the bottle in a vertical orientation relative to each other, wherein the first nail polish layer is separated from the second nail polish layer by a first film layer.
Figure 2:
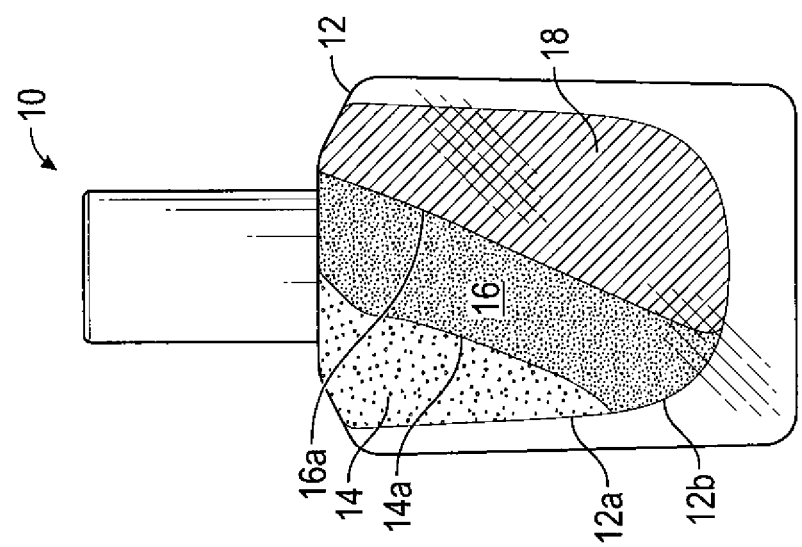
FIG. 2 is a perspective view of the nail polish composition in a nail polish bottle, showing a first nail polish layer, a second nail polish layer, and a third nail polish layer all filled in the bottle in a vertical orientation relative to each other, wherein the first nail polish layer is separated from the second and third nail polish layers by a first film layer; and wherein the second film layer separates the second nail polish layer from the third nail polish layer.
Figure 3:
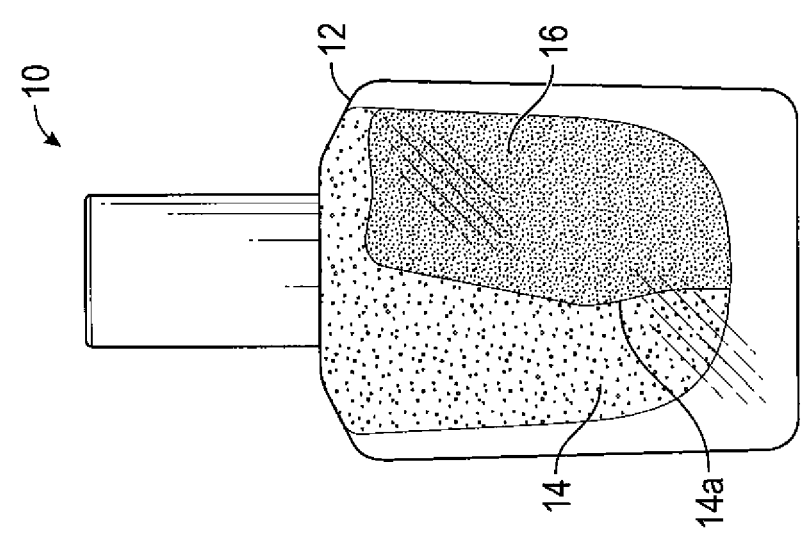
FIG. 3 is a is a perspective view of the nail polish composition in a nail polish bottle, showing a first nail polish layer, a second nail polish layer, and a third nail polish layer all filled in the bottle at angular orientations relative to each other, wherein the first nail polish layer is separated from the second and third nail polish layers by a first film layer; and wherein the second film layer separates the second nail polish layer from the third nail polish layer.

The present invention provides for a nail polish composition 10 that is filled into a nail polish bottle 12, wherein the composition comprises a first nail polish layer 14 comprising a first coloring material, which exhibits a first characteristic color, dissolved therein, and a second nail polish layer 16 comprising a second coloring material, which exhibits a second characteristic color, dissolved therein. A first film layer 14a formed over the first nail polish layer 14 separates the first and second nail polish layers 14, 16. Also, the first and second nail polish layers 14, 16 are disposed in the nail polish bottle 12 at an angle relative to each other. In this manner, the first nail polish layer 14 and the second nail polish layer 16 are immiscible. Also, the first coloring material is insoluble in the second nail polish layer 16; and the second coloring material is insoluble in the first nail polish layer 14. Further, agitation of the nail polish composition 10 causes the first and second nail polish layers 14, 16 to form an emulsion. The emulsion exhibits an apparent color that is different from the color of the first or second nail polish layers 14, 16, such that the apparent color is formed by combining the colors exhibited by the first and second coloring materials.

In alternate embodiments, the nail polish composition 10 can have a third nail polish layer 18 comprising a third coloring material, which exhibits a third characteristic color, dissolved therein. As a result, the first film layer 14a formed over the first nail polish layer 14 separates the first nail polish layer 14 from the second and third nail polish layers 16, 18. Also, a second film layer 16a formed over the second nail polish layer 16 separates the second nail polish layer 16 from said first and third nail polish layers 14, 18.

Furthermore, the third nail polish layer 18 is immiscible with said first and second nail polish layers 14, 16. Also, the third nail polish layer 18 is insoluble in the first and second nail polish layers 14, 16 and the third coloring material is insoluble in said first and second nail polish layers 14, 16. In addition, agitation of the nail polish composition 10 causes the first, second, and third nail polish layers 14, 16, 18 to form an emulsion. The resulting emulsion exhibits an apparent color that is different from the color of the first, second, or third nail polish layers 14, 16, 18, such that the apparent color is formed by combining the colors exhibited by the first, second, and third coloring materials.

Furthermore, the first, second, and third coloring materials may comprise one or several coloring materials selected from the group consisting of pigments, soluble colorants, decorative particles, nacres, and flakes.

In addition, the nail polish composition 10 may be applied to a user's nails after the three nail polish layers 14, 16, 18 are mixed or homogenized by applying the nail polish composition 10 to nails as a nail polish, as a finishing polish or as an intermediate nail polish layer. It is also understood that the three nail polish layers 14, 16, 18 each comprise different coloring materials, yet when mixed or homogenized, form a composition of a uniform appearance, with a distinct color.

In order to fill a nail polish bottle 12 with the nail polish composition 10 of the present invention, first the nail polish bottle 12 to be filled with nail polish is oriented at an angle such that it lies substantially on its side relative to a horizontal plane. Second, a first portion of the nail polish bottle 12a is filled at an angle with a first nail polish layer 14 comprising a first coloring material, which exhibits a first characteristic color, dissolved therein. Third, the first nail polish layer is left to somewhat dry or cure for preferably between 24 to 48 hours, until a first film layer 14a forms over the first nail polish layer 14. The first film layer 14a further ensures the separation of the first and second nail polish layers 14, 16. Then, the partially filled bottle is turned over at an angle onto its opposite side (relative to the horizontal plane) and a second empty portion 12b of the nail polish bottle is filled to the top of the bottle 12 with a second nail polish layer 16 comprising a second coloring material, which exhibits a second characteristic color, dissolved therein. This process results in a nail polish bottle having the appearance of a two separate blocks of different colored nail polish.

In an alternate embodiment, a third nail polish layer 18 may be added to the nail polish bottle in a similar fashion as the first and second layers 14, 16 are added to the nail polish bottle 12. Specifically, after the first two nail polish layers 14, 16 are added (with the second nail polish layer 16 being filled to an amount less than the full capacity of the bottle 12), the first and second nail polish layers 14, 16 are left to somewhat dry or cure for preferably between 24 to 48 hours, until a second film layer 16a forms over the second nail polish layer 16. Then, a third portion of the nail polish bottle 12c is filled to the top of the bottle 12 at an angle, with a third nail polish layer 18 comprising a third coloring material, which exhibits a third characteristic color, dissolved therein. This process results in a nail polish bottle having the appearance of three separate vertically arranged or angular blocks of different colored nail polish as a result of the first film layer 14a separating the first nail polish layer 14 from the second and third nail polish layers 16, 18; and the second film layer 16a separating the second nail polish layer 16 from the third nail polish layer 18.

In the specification the terms "comprise, comprises, comprised and comprising" or any variation thereof and the terms "include, includes, included and including" or any variation thereof are considered to be totally interchangeable and they should all be afforded the widest possible interpretation.

Advantages of the Present Invention

An advantage of the present invention is to provide a nail polish composition formed from different immiscible and separate layers of nail polish, wherein each separate layer exhibits a different color characteristic.

Another advantage of the present invention is to provide a nail polish composition wherein when the various layers are agitated, they combine to form a nail polish color distinct from the individual nail polish layers in the bottle.

Another advantage of the present invention is to provide a nail polish composition formed from different immiscible and separate layers of nail polish, wherein each separate layer is separated from each other by a film layer.

Another advantage of the present invention is to provide a nail polish composition formed from different immiscible and separate layers of nail polish, wherein each separate layer is filled in the nail polish bottle at an angle.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for filling a nail polish bottle with a nail polish composition, comprising the steps of:
   a) placing said nail polish bottle to be filled with nail polish at an angle relative to a horizontal plane;
   b) filling a first portion of said nail polish bottle at an angle with a first nail polish layer comprising a first coloring material, which exhibits a first characteristic color, dissolved therein;
   c) waiting until a first film layer forms over said first nail polish layer; and
   d) filling a second portion of said nail polish bottle at an angle with a second nail polish layer comprising a second coloring material, which exhibits a second characteristic color, dissolved therein; and
   e) wherein said first and second nail polish layers are separated by said first film layer.

2. A method for filling a nail polish bottle with a nail polish composition in accordance with claim 1, wherein the method comprises the steps of:
   a) waiting until a second film layer forms over said second nail polish layer;
   b) filling a third portion of said nail polish bottle at an angle with a third nail polish layer comprising a third coloring material, which exhibits a third characteristic color, dissolved therein;
   c) wherein said first film layer separates said first nail polish layer from said second and third nail polish layers; and
   d) wherein said second film layer separates said second nail polish layer from said third nail polish layer.

* * * * *